United States Patent
Alicea

(10) Patent No.: US 6,679,825 B2
(45) Date of Patent: Jan. 20, 2004

(54) PAIN ELIMINATOR

(76) Inventor: Pedro J. Alicea, 210 Benito Pérez Galdós, San Juan, PR (US) 00918

( * ) Notice: Subject to any disclaimer, the term of this patent is extended or adjusted under 35 U.S.C. 154(b) by 0 days.

(21) Appl. No.: 10/068,368

(22) Filed: Feb. 5, 2002

(65) Prior Publication Data

US 2003/0149332 A1 Aug. 7, 2003

(51) Int. Cl.⁷ .............................. A61N 2/00; A61H 5/00
(52) U.S. Cl. .............................................. 600/9; 601/15
(58) Field of Search .............................. 600/9, 612, 14, 600/15, 424; 601/15, 18, 19, 112, 113, 131, 66; 40/410; 428/3, 11; 607/3, 100, 96; 310/85, 152; 324/146; 128/897; 335/209

(56) References Cited

U.S. PATENT DOCUMENTS

| | | | | |
|---|---|---|---|---|
| 4,537,181 A | * | 8/1985 | Shalhoob et al. ............... 600/9 |
| 4,691,693 A | * | 9/1987 | Sato ............................. 601/15 |
| 4,727,857 A | * | 3/1988 | Horl ............................. 600/15 |
| 4,961,276 A | * | 10/1990 | Lin ............................... 40/410 |
| 5,085,627 A | * | 2/1992 | Fedorov et al. ................ 600/14 |
| 5,562,706 A | * | 10/1996 | Lauterbach et al. ............ 607/3 |
| 5,632,720 A | * | 5/1997 | Kleitz ........................... 601/15 |
| 6,001,055 A | * | 12/1999 | Souder ........................... 600/9 |
| 6,102,875 A | * | 8/2000 | Jones ........................... 601/113 |
| 6,124,774 A | * | 9/2000 | Quelo ........................... 335/272 |
| 6,461,377 B1 | * | 10/2002 | An ................................ 607/96 |
| 6,537,196 B1 | * | 3/2003 | Creighton et al. ............. 600/12 |

* cited by examiner

Primary Examiner—Eric F. Winakur
Assistant Examiner—Nikita R Veniaminov
(74) Attorney, Agent, or Firm—Patent Law Offices of Heath W. Hoglund

(57) ABSTRACT

A pain eliminator includes a motor, a connected axle and a set of magnets. The motor spins the magnets to generate an alternating magnetic field. This field is applied, non-invasively, to reduce muscular and other deep body pains.

16 Claims, 2 Drawing Sheets

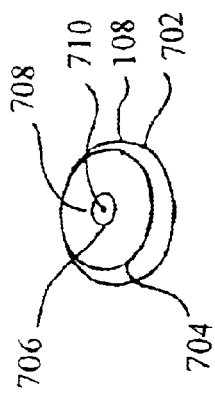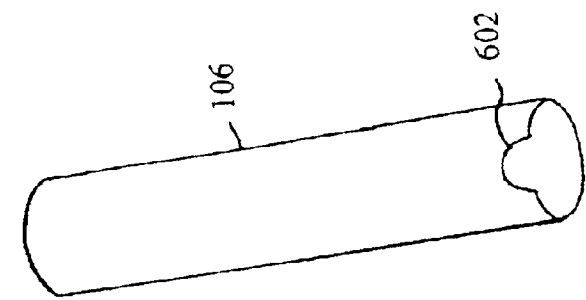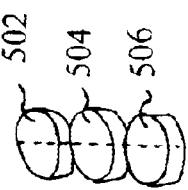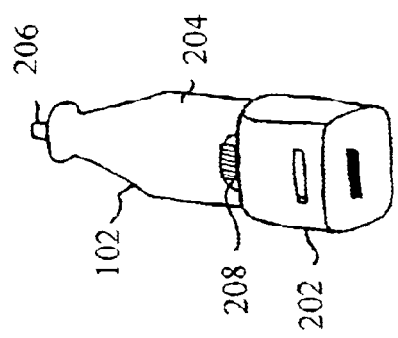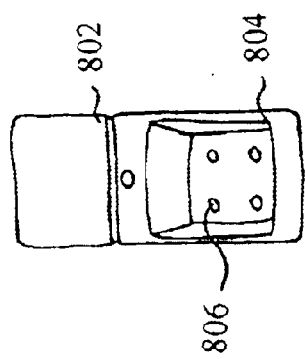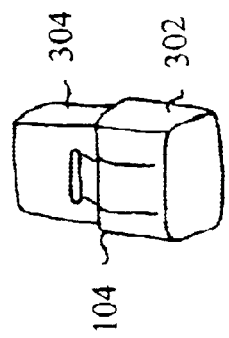

PAIN ELIMINATOR

FIELD OF THE INVENTION

The invention relates generally to a method and apparatus for reducing muscular and other deep body pains, and more particularly to a method of generating a magnetic field using rotatably driven magnets.

BACKGROUND OF THE INVENTION

Muscular and other body pains affect virtually everyone from time to time. Various treatments are used that range from temperature treatments to pharmacological treatments to physical massages. Temperature treatments heat or cool the affected area. They generally require a heat pad or ice or other source of temperature gradient. In many circumstances, a heat pad is inconvenient because it is bulky and requires a source of electricity. Ice is just as inconvenient because it melts on application. Pharmacological treatments require a prescription from a doctor. For relatively minor pains, the inconvenience of obtaining a prescription prevents needed treatment. Similarly, physicians' offices have limited availability (generally excluding evenings, weekends, holidays and other vacations). Physical massages and other in-person therapy are likewise inconvenient as they typically require making an appointment, traveling to the treatment office and waiting in turn to be treated.

Accordingly, a more convenient method and device for treating muscular and body pains is desired.

SUMMARY OF THE INVENTION

According to one aspect of the invention, a magnetic field generator especially suited to treat muscular or other deep body pains includes an electric motor, a set of round magnets, a shaft, a cylindrical housing and a cap. The electric motor has an axle capable of rotation at speeds of at least 1,000 revolutions per minute. The round magnets are substantially flat (disc-shaped) and each defines an interior channel that extends substantially across a diameter. The set of magnets are aligned so that their interior channels share a common axis. The shaft extends through the interior channel of the set of magnets. It is also attached to the axle of the electric motor so that rotation of the electric motor drives the set of magnets. The cylindrical housing has an inner diameter greater than the diameter of any of the set of round magnets. It extends from the electric motor to encase the set of magnets as well as the shaft extending through the interior channel of the set of magnets. The cap covers an outer end of the cylindrical housing.

According to further aspects of the invention, the electric motor is powered by a rechargeable battery pack electrically connected therewith and capable of powering the electric motor for at least one hour. A switch operates the electric motor, with selection between a low speed rotation and a high speed rotation. Both selections enable the electric motor to rotate at speeds of at least 1,000 rounds per minute. In one preferred embodiment, the set of magnets each have a strength of at least 1,000 gauss. In another preferred embodiment the set of magnets each have a strength of at least 10,000 gauss. The set of magnets includes three individual magnets each having the same size and strength. Each of the diameters of the set of magnets is approximately one inch and the thickness is less than one half of an inch. The cylindrical housing is composed of a plastic. The cap covering the outer end of the cylindrical housing is formed as a separate piece from the cylindrical housing. It removably engages the outer end of the cylindrical housing.

According to another aspect of the invention, a magnetic field generator is especially suited to eliminate pain. The magnetic field generator includes a plurality of magnets, an axle, an electric motor and a cover. The plurality of magnets each have a field strength of at least 10,000 gauss and define an interior channel. The plurality of magnets are arranged so that the interior channel of each of the plurality of magnets align along a common axis. The axle extends through the interior channels of the plurality of magnets and attaches to each of the plurality of the magnets. The electric motor couples with the axle and is powered to drive the axle at a speed of at least 5,000 rounds per minute. The cover defines an internal cavity and connecting with the electric motor to enclose the plurality of magnets so that rotation of the plurality of magnets is concealed.

According to another aspect of the invention, a magnetic field generator is provided to eliminate pain. It is repeatedly passed over a treatment area affected by pain.

BRIEF DESCRIPTION OF THE DRAWINGS

FIG. 2 is a perspective view of the motor 102 of FIG. 1, shown apart from the pain eliminator 100.

FIG. 3 is a perspective view of the battery pack 104 of FIG. 1, shown apart from the pain eliminator 100.

FIG. 4 is a perspective view of an axle 400 contained within cover 106 of FIG. 1, shown apart from the pain eliminator 100.

FIG. 5 is a perspective view of three magnets 502, 504 and 506 also contained within cover 106 of FIG. 1, shown apart from the pain eliminator 100.

FIG. 6 is a perspective view of the cover 106 of FIG. 1, shown apart from the pain eliminator 100.

FIG. 7 is a perspective view of the cap 108 of FIG. 1, shown apart from the pain eliminator 100.

FIG. 8 is a perspective view of a charger used to recharge battery pack 104.

DETAILED DESCRIPTION OF THE INVENTION

Figure 1:
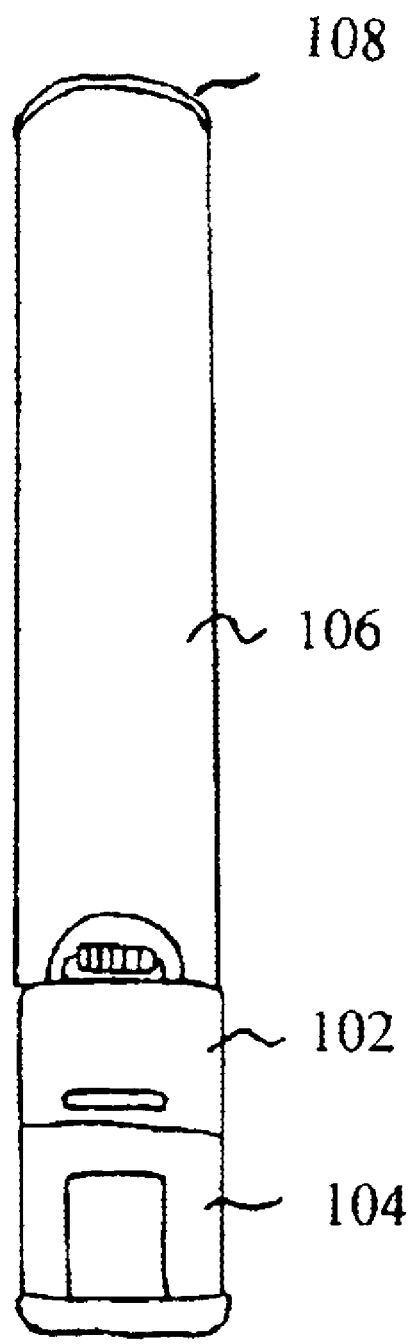
FIG. 1 is perspective view of one preferred pain eliminator 100 including a motor 102, a battery pack 104, a cover 106, a cap 108.

The pain eliminator operates by creating an alternating magnetic field at high speeds along the surface of the body. Although the pain eliminator only passes over the surface of the body, the alternating magnetic field that it generates penetrate below the surface to reach muscular or other deep body pains. This non-invasive method has proven effective at eliminating inflammation and pain. It has proven particularly effective against muscular pains, sciatica pains, muscle cramps and spasms, fibromyalgia pains, arthritis pains, back pains, and ligament pains. In addition to eliminating pain, this treatment also has proven effective at soothing, reducing tension and stress.

The pain eliminator also solves many of the problems of other types of treatment. It is a lightweight, hand-held and totally portable. It can be carried in a sports pack, purse or any other bag. Consequently, it is available at any time of the day, any day of the year, and anywhere a person wishes to carry it.

Preferably the pain eliminator is activated. The pain eliminator is held in close proximity to or in direct contact with the patient's skin proximate the treatment area. The pain eliminator is moved about the treatment area for an extended period of time, preferably at least one half of an hour. This action eliminates many inner body pains.

Turning to FIG. 1, one preferred embodiment is described. It includes motor 102, which is enclosed in a casing. The motor is preferably able to operate at speeds of at least 5,000 rounds per minute (rpm). Motor 102 engages batteries 104, which are also enclosed in a casing. The batteries 104 are capable of powering the motor for at least one hour of operation and more preferably at least one and a half hours. Motor 102 engages an axle and magnets (not shown) encased by cover 106. The axle connects the motor 102 to the magnets so that operation of motor 102 spins the magnets rapidly to generate an alternating magnetic field. Cover 106 engages motor 102 on its bottom end. This forms a rigid connection. Cover 106 is closed on its top end by a cap 108. This also forms a rigid connection with cover 106.

Turning to FIGS. 2–8, the individual pieces of the pain eliminator are shown and described. With reference to FIG. 2, the motor 102 includes a base 202 that is used to engage batteries 104. The motor itself is housed within a round plastic casing 204. The plastic casing 204 tapers to an axle joint 206. Axle joint 206 connects the motor 102 with the axle that rotates the magnets. Switch 208 permits selection between on and off. In the on position, the motor rotates at 5,000 rpm. Alternatively, a three-position (high, low and off) switch could be used. In the high setting the motor rotates at 10,000 rpm, and in the medium setting the motor rotates at 5,000 rpm. The switch extends from the plastic casing 204 proximate base 202.

Turning to FIG. 3, batteries 104 are shown apart from the pain eliminator. Batteries 104 are held in a plastic case 302 that engages base 202. The plastic case 302 is substantially rectangular in shape. The plastic case 302 narrows to form a body portion 304. This fits within base 202.

Turning to FIG. 4, one preferred axle 400 is shown. It is a simple straight rod. It connects with axle joint 206 so that the rotation of motor 102 rotates axle 400. Axle 400, in turn passes through and connects with the magnets to create an alternating magnetic field.

Turning to FIG. 5, one preferred set of magnets is shown. The set includes magnets 502–504. Alternatively, sets of two, four or more could be used. Magnets 502–504 are each round, preferably approximately one inch in diameter and approximately three-eights inch thick. Magnets 502–504 each have a strength of approximately 12,000 gauss. Magnets 502–504 each define an interior channel, shown as a phantom line. It passes along a diameter of each of the magnets 502–504. The interior channel is also centered along the thickness of each of the magnets. The interior channel runs parallel to the outer round faces of the magnets 502–504. Axle 400 passes through and engages the interior channels. In operation, the face of the magnets 502 are aligned along a common plane. The interior channels align along a common axis.

Cover 106 houses the magnets 502–504 and engages motor 102. It is cylindrical with an inner diameter greater than the diameter of the magnets 502–504. Three screws around the bottom perimeter of cover 106 fixedly attach cover 106 to motor 102. The bottom of cover 106 also defines a notch 602. The notch 602 is aligned with switch 208. When cover 106 is joined with motor 102, switch 208 extends through notch 602 so that it remains accessible.

Cap 108 is used to close the top of cover 106 and to provide an upper pivot point for axle 400. More specifically, cap 108 is formed of an outer disc 702 having the largest diameter. This diameter is approximately the same as the outer diameter of the cover 106. A middle disc 704 extends from outer disc 702. It is approximately the same size as the inner diameter of cover 106. When cap 108 is positioned on top of cover 106, this middle disc forms a friction fit with the inner surface of cover 106. In addition, three screws extending through the top of cover 106 engage and hold cap 108. Inner disc 706 extends from middle disc 704. It is substantially smaller in diameter. At its center, inner disc holds a bearing 708 that defines a dimple 710 that is used as an upper pivot point for axle 400. Preferably bearing 708 is a ball bearing to provide a long and reliable useful life. However, other bearings or bushings may be used especially where cost is a limiting consideration.

FIG. 8 shows a battery charger 802. The battery charger 802 defines a holster 804 that receives batteries 104. Holster 804 includes four charging prongs that pass charging electricity to the batteries 104. Periodically, preferably after each use, the pain eliminator should be recharged.

Although the pain eliminator has been described with reference to a specific preferred embodiment, those skilled in the art will appreciate that many variations and modifications are possible without departing from the spirit and scope of the invention. All such variations and modifications are intended to be encompassed within the scope of the following claims.

I claim:

1. A magnetic field generator especially suited to treat muscular or other deep body pains comprising:
   an electric motor having an axle capable of rotation at speeds of least 1,000 rounds per minute;
   a set of round and flat magnets each defining an interior channel extending substantially across a diameter, wherein the set of magnets are aligned so that their interior channels share a common axis;
   a shaft extending through the interior channel of the set of magnets and attached thereto, and further attached to the axle of the electric motor so that rotation of the electric motor drives the set of magnets;
   a cylindrical housing having an inner diameter greater than the diameter of any of the set of round magnets and configured to extend from the electric motor to encase the set of magnets as well as the shaft extending through the interior channel of the set of magnets; and
   a cap covering an outer end of the cylindrical housing.

2. The magnetic field generator of claim 1, wherein the electric motor further comprises a rechargeable battery pack electrically connected with the electric motor and capable of powering the electric motor for at least one hour.

3. The magnetic field generator of claim 1, wherein the electric motor further comprises a switch having a selection between a low speed rotation and a high speed rotation, wherein both selections enable the electric motor to rotate at speeds of at least 1,000 rounds per minute.

4. The magnetic field generator of claim 1, wherein the set of magnets each have a strength of at least 1,000 gauss.

5. The magnetic field generator of claim 4, wherein the set of magnets comprises three magnets, and wherein each of the diameters of the set of magnets is approximately one inch and the thickness is less than one half of an inch.

6. The magnetic field generator of claim 1, wherein the set of magnets each have a strength of at least 10,000 gauss.

7. The magnetic field generator of claim 1, wherein the set of magnets each share the same dimensions.

8. The magnetic field generator of claim 1, wherein the cylindrical housing is composed of a plastic.

9. The magnetic field generator of claim 1, wherein the cap covering the outer end of the cylindrical housing is formed as a separate piece from the cylindrical housing and removably engages the outer end of the cylindrical housing.

10. A magnetic field generator especially suited to eliminate pain comprising:
- a plurality of magnets each having a field strength of at least 10,000 gauss and defining an interior channel, wherein the plurality of magnets are arranged so that the interior channel of each of the plurality of magnets align along a common axis;
- an axle extending through the interior channels of the plurality of magnets and attaching to each of the plurality of the magnets;
- an electric motor coupled with the axle and powered to drive the axle at a speed of at least 5,000 rounds per minute;
- a cover defining an internal cavity and connecting with the electric motor to enclose the plurality of magnets so that rotation of the plurality of magnets is concealed.

11. The magnetic field generator of claim 10, wherein the plurality of magnets comprise three circular magnets each the same size and having a diameter substantially greater than a thickness of the circular magnets, and wherein the interior channel extends across the diameter of each of the plurality of magnets.

12. The magnetic field generator of claim 10, wherein the axle forms a friction fit with the interior channel of each of the plurality of magnets so that rotation of the axle drives rotation of the plurality of magnets.

13. The magnetic field generator of claim 10, wherein the electric motor is powered by a rechargeable battery capable of operation for at least on hour.

14. The magnetic field generator of claim 10, wherein the cover is substantially cylindrical and sized so that an interior diameter of the cover is greater than the cross section of any of the plurality of magnets.

15. The magnetic field generator of claim 14, wherein the plurality of magnets comprise three circular magnets each the same size and having a diameter less than the interior diameter of the cover.

16. A method of treating body pains by application of an alternating magnetic field comprising the steps of:
- providing a magnetic field generator that comprises:
  - a plurality of magnets each having a field strength of at least 10,000 gauss and defining an interior channel, wherein the plurality of magnets are arranged so that the interior channel of each of the plurality of magnets align along a common axis;
  - an axle extending through the interior channels of the plurality of magnets and attaching to each of the plurality of the magnets;
  - an electric motor coupled with the axle and powered to drive the axle at a speed of at least 5,000 rounds per minute; and
  - a cover defining an internal cavity and connecting with the electric motor to enclose the plurality of magnets so that rotation of the plurality of magnets is concealed;
- activating the magnetic field generator so that the plurality of magnets rotate to generate an alternating magnetic field; and
- repeatedly passing the magnetic field generator over a treatment area affected by pain.

* * * * *